United States Patent
Kornek et al.

(10) Patent No.: US 7,208,618 B2
(45) Date of Patent: *Apr. 24, 2007

(54) CONTINUOUS PRODUCTION OF ORGANOSILANES

(75) Inventors: Thomas Kornek, Burghausen (DE); Andreas Bauer, Simbach (DE); Diana Senden, Burghausen (DE)

(73) Assignee: Wacker Chemie AG, Munich (DE)

( * ) Notice: Subject to any disclaimer, the term of this patent is extended or adjusted under 35 U.S.C. 154(b) by 122 days.

This patent is subject to a terminal disclaimer.

(21) Appl. No.: 10/521,377

(22) PCT Filed: Jun. 12, 2003

(86) PCT No.: PCT/EP03/06204

§ 371 (c)(1), (2), (4) Date: Jan. 18, 2005

(87) PCT Pub. No.: WO2004/009607

PCT Pub. Date: Jan. 29, 2004

(65) Prior Publication Data

US 2005/0240043 A1    Oct. 27, 2005

(30) Foreign Application Priority Data

Jul. 18, 2002   (DE) ................ 102 32 663

(51) Int. Cl.
*C07F 7/04*   (2006.01)

(52) U.S. Cl. ...................... 556/466; 556/136

(58) Field of Classification Search ........... 556/466, 556/136

See application file for complete search history.

(56) References Cited

U.S. PATENT DOCUMENTS

| 4,658,050 | A | | 4/1987 | Quirk et al. | |
|---|---|---|---|---|---|
| 5,616,762 | A | * | 4/1997 | Kropfgans et al. | 556/479 |
| 6,359,161 | B2 | * | 3/2002 | Tonomura et al. | 556/479 |
| 6,388,119 | B1 | * | 5/2002 | Bauer et al. | 556/479 |
| 2002/0052520 | A1 | | 5/2002 | Bauer et al. | |

FOREIGN PATENT DOCUMENTS

| DE | 195 34 853 A1 | 5/1996 |
|---|---|---|
| DE | 100 53 037 C1 | 1/2002 |
| EP | 0 239 677 | 10/1987 |
| EP | 1 156 052 A2 | 11/2001 |
| EP | 1 201 671 A1 | 5/2002 |
| JP | 07-126271 | 5/1995 |

OTHER PUBLICATIONS

Apple et al., Iridium Complexes as Hydrosilylation Catalysts, Journal of Molecular Catalysis, 29, 1985, 55-64.*
Derwent Abstract corresponding to DE 100 53 037.
Derwent Abstract corresponding to JP 07-126271.

* cited by examiner

*Primary Examiner*—Thurman K. Page
*Assistant Examiner*—Chukwuma Nwaonicha
(74) *Attorney, Agent, or Firm*—Brooks Kushman P.C.

(57) ABSTRACT

Preparation of organosilanes by hydrosilylation of an alkene takes place in a continuous manner using an iridium hydrosilylation catalyst and diene cocatalyst. The continuous process provides high yields in a safe and economical manner.

13 Claims, No Drawings

CONTINUOUS PRODUCTION OF ORGANOSILANES

BACKGROUND OF THE INVENTION

1. Field of the Invention

The invention relates to a process for the continuous preparation of organosilanes by hydrosilylation in the presence of an iridium compound as catalyst and free diene as cocatalyst.

2. Description of the Invention

Substituted alkylsilanes are of tremendous economic importance in many fields. They are used, for example, as adhesion promoters or as crosslinkers.

The platinum- or rhodium-catalyzed hydrosilylation of unsaturated compounds has been widely studied in the past. The product yields are often very low, being only 20–45%, which is attributable to considerable secondary reactions.

Iridium catalysts containing diene ligands are, according to U.S. Pat. No. 4,658,050, used in the hydrosilylation of allyl compounds with alkoxy-substituted silanes. JP-A-07126271 describes the hydrosilylation of allyl halides using chlorodimethylsilane in the presence of iridium catalysts containing diene ligands. Disadvantages of these processes are either moderate yields, an uneconomically high catalyst concentration and/or a very short catalyst life. Although EP-A-1156052 and DE-C-10053037 describe the addition of additional diene ligands to increase the catalyst life, the processes in all cases mentioned are batch processes which are subject to very unfavorable preconditions both from an economic point of view and an engineering and safety point of view because of the strongly exothermic character of hydrosilylation reactions, which creates the risk of the reaction becoming "dormant" and later starting up again with a sudden, extremely high generation of heat and pressure.

SUMMARY OF THE INVENTION

It is therefore an object of the invention to develop a process which gives high product yields and purities and, in particular, takes account of the aspects of economic and especially engineering and safety considerations in the preparation of organosilanes by hydrosilylation. These and other object are achieved by the present invention.

DETAILED DESCRIPTION OF THE PREFERRED EMBODIMENT(S)

The invention provides a process for the continuous preparation of a silane of the formula I $$R^6R^5CH-R^4CH-SiR^1R^2R^3 \quad (I),$$

which comprises continuously reacting a silane of the formula II $$HSiR^1R^2R^3 \quad (II),$$

with an alkene of the formula III $$R^6R^5C=CHR^4 \quad (III),$$

in the presence of an iridium compound of the formula IV as catalyst $$[(diene)IrCl]_2 \quad (IV),$$

and free diene as cocatalyst, where $R^1$, $R^2{}_1$, $R^3$ are each a monovalent Si—C-bonded, unsubstituted or halogen-substituted $C_1$–$C_{18}$-hydrocarbon radical, a chlorine atom or a $C_1$–$C_{18}$-alkoxy radical, $R^4$, $R^5$, $R^6$ are each a hydrogen atom, a monovalent $C_1$–$C_{18}$-hydrocarbon radical which may be unsubstituted or bear F, Cl, OR, $NR'_2$, CN or NCO atoms/groups as substituents, a chlorine atom, a fluorine atom or a $C_1$–$C_{18}$-alkoxy radical, where in each case 2 radicals $R^4$, $R^5$, $R^6$ together with the carbon atoms to which they are bound may form a cyclic radical, R is a hydrogen atom or a monovalent $C_1$–$C_{18}$-hydrocarbon radical and diene is a $C_4$–$C_{50}$-hydrocarbon compound which may be unsubstituted or bear F, Cl, OR, $NR_2$, CN or NCO atoms/groups as substituents and has at least two ethylenic C=C double bonds, with the reaction temperature being 30–200° C. and the reaction pressure being 0.11–50.0 Mpa.

The continuous process gives the silane of the formula I in high yields and excellent purity.

In this process, the target products of the formula I are obtained in yields of from at least 95% up to 98% when using very small amounts of catalyst. Depending on the field of application, work-up by distillation can therefore be dispensed with.

The process is easy to control and can be carried out safely.

Suitable engineering embodiments for carrying out the process are all customary reactors for carrying out reactions continuously, i.e., for example, tube and loop reactors and also continuously operated stirred reactors.

In terms of the order in which the reaction components are introduced, all conceivable combinations are possible; in particular, the components can be partly premixed before introduction into the reactor. The catalyst is preferably not present in an environment comprising an excess of silane of the formula II over the alkene of the formula III, since this can otherwise display deactivation.

$C_1$–$C_{18}$-hydrocarbon radicals $R^1$, $R^2$, $R^3$ are preferably alkyl, alkenyl, cycloalkyl or aryl radicals. $R^1$, $R^2$, $R^3$ preferably have not more than 10, in particular not more than 6, carbon atoms. $R^1$, $R^2$, $R^3$ are preferably linear or branched $C_1$–$C_6$-alkyl radicals or $C_1$–$C_6$-alkoxy radicals. Preferred halogen substituents are fluorine and chlorine. Particularly preferred radicals $R^1$, $R^2$, $R^3$ are methyl, ethyl, methoxy, ethoxy, chlorine, phenyl and vinyl.

Hydrocarbon radicals $R^4$, $R^5$, $R^6$ are preferably alkyl, alkenyl, cycloalkyl or aryl radicals. It is preferred that not more than one of $R^4$, $R^5$, $R^6$ is an alkoxy radical. $R^5$, $R^6$ preferably have not more than 10, in particular not more than 6, carbon atoms. $R^5$, $R^6$ are preferably linear or branched $C_1$–$C_6$-alkyl radicals or $C_1$–$C_6$-alkoxy radicals. Particularly preferred radicals $R^5$, $R^6$ are hydrogen, methyl, ethyl, chlorine and phenyl.

The hydrocarbon radical $R^4$ preferably has not more than 6, in particular not more than 2, carbon atoms. Particularly preferred radicals $R^4$ are hydrogen, methyl, ethyl.

The hydrocarbon radical R preferably has not more than 6, in particular not more than 2, carbon atoms.

The hydrocarbon compounds used as diene may comprise not only the molecular units containing ethylenic C=C double bonds but also alkyl, cycloalkyl or aryl units. The dienes preferably have from 6 to 12 carbon atoms. Preference is given to monocyclic or bicyclic dienes. Preferred examples of dienes are butadiene, 1,3-hexadiene, 1,4-hexadiene, 1,5-hexadiene, isoprene, 1,3-cyclohexadiene, 1,3-cyclooctadiene, 1,4-cyclooctadiene, 1,5-cyclooctadiene and norbornadiene.

The diene in the catalyst of the formula IV and the free diene serving as cocatalyst can be identical or different. Preference is given to the two dienes being identical.

In a particularly preferred case, the catalyst of the formula IV used is [(cycloocta-1c,5c-diene)IrCl]$_2$ and the cocatalyst used is 1,5-cyclooctadiene.

The alkene of the formula III is preferably used in an excess of from 0.01 to 100 mol % of II, particularly preferably from 0.1 to 10 mol %, based on the silane component of the formula II. The iridium compound of the formula IV is preferably present in a concentration of from $1\times10^{-6}$ to $1\times10^{-1}$ mol %, in particular from $1\times10^{-4}$ to $1\times10^{-2}$ mol %, based on the silane component of the formula II. The diene as cocatalyst is preferably added in a concentration of from $1\times10^{-6}$ to 1 mol %, in particular from $1\times10^{-3}$ to $1\times10^{-1}$ mol %, based on the silane component of the formula II as cocatalyst.

The process can be carried out in the presence or absence of aprotic solvents. If aprotic solvents are used, solvents or solvent mixtures having a boiling point or boiling range up to 120° C. at 0.1 MPa are preferred. Examples of such solvents are ethers such as dioxane, tetrahydrofuran, diethyl ether, diisopropyl ether, diethylene glycol dimethyl ether; chlorinated hydrocarbons such as dichloromethane, trichloromethane, tetrachloromethane, 1,2-dichloroethane, trichloroethylene; hydrocarbons such as pentane, n-hexane, hexane isomer mixtures, heptane, octane, naphtha, petroleum ether, benzene, toluene, xylenes; ketones such as acetone, methyl ethyl ketone, diisopropyl ketone, methyl isobutyl ketone (MIBK); esters such as ethyl acetate, butyl acetate, propyl propionate, ethyl butyrate, ethyl isobutyrate; carbon disulfide and nitrobenzene, or mixtures of these solvents.

The target product of the formula I can also be used as aprotic solvent in the process. This process variant is preferred.

The process is preferably carried out at a reaction temperature of 60–100° C., particularly preferably 75–85° C. The reaction pressure is preferably 0.2–1.5 MPa, particularly preferably 0.4–0.5 MPa.

For example, the reaction components of the formula II as one feed stream and the reaction components of the formula III together with iridium catalyst of the formula IV, if appropriate in admixture with the diene, as second feed stream are fed continuously into a loop reactor. In another variant, the reactor is started up by initially charging it with the target product of the formula I or an abovementioned solvent together with catalyst of the formula IV and, if appropriate, diene and continuously feeding a mixture of component III and, if appropriate, diene as one feed stream and the component of the formula II as second feed stream continuously into the reactor. The mean residence times of the reactor contents are preferably from 5 to 60 minutes, in particular from 10 to 40 minutes, particularly preferably from 25 to 30 minutes.

The meanings of all the symbols in the formulae above are in each case independent of one another.

In the following examples, all concentrations and percentages are by weight, all pressures are 0.10 MPa (abs.) and all temperatures are 20° C. unless indicated otherwise.

EXAMPLE 1

Dimethylchlorosilane as one feed stream and a mixture of $2.7\times10^{-3}$ mol % of di-μ-chlorobis[(cycloocta-1c,5c-diene) iridium(I)] and $7\times10^{-1}$ mol % of 1,5-cyclooctadiene in allyl chloride as a second feed stream were fed in a molar ratio of silane:allyl chloride mixture of 1:1.05 at a rate of 2.8 l/h (based on the total volume of the components introduced) via separate metering pumps into a loop reactor maintained at 80° C. under a pressure of 0.4 MPa and having a volume of 1.4 l. After working up the crude mixture by distillation using a thin film evaporator to separate off the catalyst and the excess of allyl chloride, chloro(3-chloropropyl)dimethylsilane was obtained in a yield of 95% and a purity of >99% based on the silane.

EXAMPLE 2

Example 1 was repeated with the modification that the reactor was operated at 50° C. and a pressure of 0.2 MPa and the reactants were fed in at a rate of 2.1 l/h (based on the total volume of the components introduced). After working up the crude mixture by distillation using a thin film evaporator to separate off the catalyst and the excess of allyl chloride, chloro(3-chloropropyl)dimethylsilane was obtained in a yield of 95% and a purity of >99% based on the silane.

EXAMPLE 3

Example 1 was repeated with the modification that the reactor was operated at 100° C. and a pressure of 1.0 MPa and the reactants were fed in at a rate of 5.6 l/h (based on the total volume of the components introduced). After working up the crude mixture by distillation using a thin film evaporator to separate off the catalyst and the excess of allyl chloride, chloro(3-chloropropyl)dimethylsilane was obtained in a yield of 95% and a purity of >99% based on the silane.

EXAMPLE 4

Example 1 was repeated with the modification that the reactor was operated at 130° C. and a pressure of 1.0 MPa and the reactants were fed in at a rate of 5.6 l/h (based on the total volume of the components introduced). After working up the crude mixture by distillation using a thin film evaporator to separate off the catalyst and the excess of allyl chloride, chloro(3-chloropropyl)dimethylsilane was obtained in a yield of 95% and a purity of >99% based on the silane.

EXAMPLE 5

Example 1 was repeated with the modification that the reactants were fed in in a molar ratio of silane:allyl chloride mixture of 1:1. After working up the crude mixture by distillation using a thin film evaporator to separate off the catalyst, chloro(3-chloropropyl)-dimethylsilane was obtained in a yield of 95% and a purity of >99% based on the silane.

EXAMPLE 6

Example 1 was repeated with the modification that the reactants were fed in in a molar ratio of silane:allyl chloride mixture of 1:1.3. After working up the crude mixture by distillation using a thin film evaporator to separate off the catalyst and the excess of allyl chloride, chloro(3-chloropropyl)dimethylsilane was obtained in a yield of 95% and a purity of >99% based on the silane.

EXAMPLE 7

Example 1 was repeated with the modification that $1 \times 10^{-4}$ mol % of di-μ-chlorobis[(cycloocta-1c,5c-diene)-iridium(I)] and $1 \times 10^{-3}$ mol % of 1,5-cyclooctadiene were used. After working up the crude mixture by distillation using a thin film evaporator to separate off the catalyst and the excess of allyl chloride, chloro(3-chloropropyl)dimethylsilane was obtained in a yield of 95% and a purity of >99% based on the silane.

EXAMPLE 8

Example 1 was repeated with the modification that toluene was placed in the reactor as solvent before commencement of the metered addition. After working up the crude mixture by distillation using a thin film evaporator to separate off the catalyst and the excess of allyl chloride, chloro(3-chloropropyl)dimethylsilane was obtained in a yield of 95% and a purity of >99% based on the silane.

EXAMPLE 9

Example 1 was repeated with the modification that a tube reactor was used in place of the loop reactor. After working up the crude mixture by distillation using a thin film evaporator to separate off the catalyst and the excess of allyl chloride, chloro(3-chloropropyl)dimethylsilane was obtained in a yield of 95% and a purity of >99% based on the silane.

EXAMPLE 10

Example 1 was repeated with the modification that the high-boiling residue obtained in the isolation of the product was used in place of a freshly prepared catalyst/cocatalyst mixture. After working up the crude mixture by distillation using a thin film evaporator to separate off the catalyst and the excess of allyl chloride, chloro(3-chloropropyl)dimethylsilane was obtained in a yield of 95% and a purity of >99% based on the silane.

The invention claimed is:

1. A process for the continuous preparation of a silane of the formula I $$R^6R^5CH-R^4CH-SiR^1R^2R^3 \quad (I),$$

which comprises continuously reacting a silane of the formula II $$HSiR^1R^2R^3 \quad (II),$$

with an alkene of the formula III $$R^6R^5C=CHR^4 \quad (III),$$

in the presence of an iridium compound of the formula IV as catalyst $$[(diene)IrCl]_2 \quad (IV),$$

and free diene as cocatalyst, where
- $R^1$, $R^2$, $R^3$ are each a monovalent Si—C-bonded, unsubstituted or halogen-substituted $C_1$–$C_{18}$-hydrocarbon radical, a chlorine atom or a $C_1$–$C_{18}$-alkoxy radical,
- $R^4$, $R^5$, $R^6$ are each a hydrogen atom, a monovalent $C_1$–$C_{18}$-hydrocarbon radical optionally bearing one or more F, Cl, OR, NR'$_2$, CN or NCO substituents, a chlorine atom, a fluorine atom or a $C_1$–$C_{18}$-alkoxy radical, where 2 radicals $R^4$, $R^5$, $R^6$ together with the carbon atoms to which they are bound may form a cyclic radical,
- R is a hydrogen atom or a monovalent $C_1$–$C_{18}$-hydrocarbon radical and
- diene is a $C_4$–$C_{50}$-hydrocarbon compound optionally bearing one or more F, Cl, OR, NR$_2$, CN or NCO substituents and has at least two ethylenic C=C double bonds, with the reaction temperature being 30–200° C. and the reaction pressure being 0.11–50.0 Mpa, in a mol ratio of alkene (III) to silane (II) such that 0.01 to 100 mol % of (III) is present in excess over (II) when said catalyst is present.

2. The process of claim 1, wherein $R^1$, $R^2$ and $R^3$ are $C_1$–$C_6$-alkyl radicals, $C_1$–$C_6$-alkoxy radicals, or mixtures thereof.

3. The process of claim 1, wherein $R^5$ and $R^6$ are $C_1$–$C_6$-alkyl radicals, $C_1$–$C_6$-alkoxy radicals, or mixtures thereof.

4. The process of claim 1, wherein $R^4$ is selected from the group consisting of hydrogen, methyl, and ethyl.

5. The process of claim 1, wherein free diene is added as cocatalyst in a concentration of from $1 \times 10^{-6}$ to 1 mol %, based on the silane component of the formula II.

6. The process of claim 1, wherein the reaction temperature is 60–100° C.

7. The process of claim 1, wherein the catalyst of the formula IV is [(cycloocta-1c,5c-diene)IrCl]$_2$.

8. The process of claim 7, wherein the cocatalyst is 1,5-cyclooctadiene.

9. The process of claim 1, wherein the alkene of formula (III) is present in 0.1 mol percent to 10 mol percent stoichiometric excess relative to the silane of formula (II).

10. The process of claim 1, wherein reacting takes place in an aprotic solvent.

11. The process of claim 1, wherein the aprotic solvent comprises silane (I).

12. The process of claim 1, further comprising separating silane (I) and leaving a high boiling residue, and recycling at least a portion of the high boiling residue as catalyst to the step of reacting.

13. The process of claim 1 wherein the free diene is not the same as the diene of the catalyst (IV).

* * * * *

UNITED STATES PATENT AND TRADEMARK OFFICE
CERTIFICATE OF CORRECTION

| | | |
|---|---|---|
| PATENT NO. | : 7,208,618 B2 | Page 1 of 1 |
| APPLICATION NO. | : 10/521377 | |
| DATED | : April 24, 2007 | |
| INVENTOR(S) | : Thomas Kornek et al. | |

It is certified that error appears in the above-identified patent and that said Letters Patent is hereby corrected as shown below:

Column 6, Line 45, Claim 11:

Delete "1" and insert therefor -- 10 --.

Signed and Sealed this

Twenty-fourth Day of July, 2007

JON W. DUDAS
*Director of the United States Patent and Trademark Office*